United States Patent [19]

Garner

[11] Patent Number: 5,731,416

[45] Date of Patent: Mar. 24, 1998

[54] PEPTIDE BASED NUCLEIC ACID SURROGATES

[75] Inventor: Philip P. Garner, Cleveland Heights, Ohio

[73] Assignee: Case Western Reserve University, Cleveland, Ohio

[21] Appl. No.: 645,930

[22] Filed: May 14, 1996

Related U.S. Application Data

[63] Continuation of Ser. No. 144,705, Oct. 28, 1993, abandoned.
[51] Int. Cl.$^6$ .............................. C07K 2/00; A61K 38/02
[52] U.S. Cl. ............................ 530/350; 514/2; 514/44; 536/23.1; 536/24.3; 536/24.1
[58] Field of Search ..................... 536/24.1, 23.1; 530/300; 514/44, 2

[56] References Cited

PUBLICATIONS

Garner et al., Tetrahedron Letters 34, pp. 1275–1278 (1993).
Weller et al., J. Org. Chem 56, pp. 6000–6006 (1991).
Timoshch et al, Zh. Obschch. Khim. 58(1988), p. 2140.
Uhlmann et al., Chemical Reviews 90(1990), pp. 544–584.
Plattner et al., in *Drug Discovery Technologies*, 1990, Ellis Harwood Limited, pp. 92–126.
Tyaglow, B.V. et al., Zh. Obshch. Khim. (1987) 57, 2124.
Hyrup et al., "Structure–activity studies of the binding of modified peptide nucleic acids (PNAs) to DNA", J. Am. Chem. Soc. 116: 7964–7970, 1994.

*Primary Examiner*—Jasemine C. Chambers
*Assistant Examiner*—Scott D. Priebe
*Attorney, Agent, or Firm*—Fay, Sharpe, Beall, Fagan, Minnich & McKee

[57] ABSTRACT

The present invention relates to the development of a new class of oligonucleotide surrogates capable of sequence specific binding to simple stranded DNA and RNA as well as to double stranded DNA targets. More specifically, structures $(Ser/Thr[CH_2B]-AA)_n$ represent the repeating structural units for a number of the nucleic acid surrogates of the present invention. Once synthesized (in suitably protected form), the monobasic units are linked together via peptide bonds to produce the required oligomeric structures having defined nucleobase sequences. These nucleic acid surrogates may then be utilized for use as antisense/antigene probes and/or drug carriers.

13 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: irrelevant ( i x ) FEATURE:
        ( D ) OTHER INFORMATION: Xaa represents serine modified with the addition of a pyridine base.

( v i ) SEQUENCE DESCRIPTION: SEQ ID NO: 1:

Xaa Gly Xaa Gly ( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: irrelevant ( i v ) ANTI-SENSE: no ( v ) SEQUENCE DESCRIPTION: SEQ ID NO: 2:

Ser Gly Ser Gly Ser Gly Ser Gly Ser Gly Ser Gly Ser Gly Ser Gly Lys
             5                10             15

PEPTIDE BASED NUCLEIC ACID SURROGATES

This is a continuation of application Ser. No. 08/144,705, filed Oct. 28, 1993, now abandoned.

FIELD OF THE INVENTION

The present invention relates to the synthesis of new peptide nucleic acids (PNAs) and peptide-based nucleic acid surrogates. The new peptide-based nucleic acid surrogates are capable of sequence specific binding to single stranded DNA and RNA as well as to double stranded DNA targets. In addition, the present invention is directed to the use of the new peptide-based nucleic acid surrogates as antisense/antigene probes and/or as drug carriers.

BACKGROUND OF THE INVENTION

The discovery that translation (protein synthesis) could be effectively inhibited by endogenous antisense RNAs and DNAs suggested that this principle might have wide-ranging therapeutic potential. For selective inhibition of gene expression, one need only know the base sequence of a particular mRNA target to synthesize its antisense nucleic acid complement. This antisense nucleic acid can either be produced in vivo genetically or ex vivo which then requires transport into the targeted cell. Duplex formation between the antisense agent and the target RNA strand prevents translation by disrupting the ribosomal machinery or, with oligodeoxynucleotides, by RNase degradation of the mRNA-antisense DNA duplex. Inhibition is also possible at the DNA level via triplex formation (so-called antigene inhibition) even though the same degree of sequence-specificity has not yet been achieved. In theory, an oligomer containing 11–15 bases is sufficient for single gene resolution at the RNA level in humans.

It is now well-recognized that, by targeting known oncogenes, the antisense strategy can be used to help elucidate the mechanism of tumorigenesis and, at the same time, serve as the basis of new anticancer chemotherapies. (Hélène, C. "Rational Design of Sequence-specific Oncogene Inhibitors Based on Antisense and Antigene Oligonucleotides" Eur. J. Cancer, 1991, 27, 1466; and, Prospects for Antisense Nucleic Acid Therapy of Cancer and Aids, Wickstrom, E. Ed.; Wiley-Liss: New York, 1991). Thus, it has been shown that the expression of mRNAs corresponding to the myc (Szczylik, C.; Skorsky, T.; Nicolaides, N. C., et at. "Selective Inhibition of Leukemia Cell Proliferation by BCR-ABL Antisense Oligonucleotides" Science 1991, 253, 562), myb (Anfossi, G.; Gewirtz, A. M.; Calabretta, B. "An Oligomer Complimentary to c-myb-Encoded mRNA inhibits Proliferation of Human Myeloid Leukemia Cell Lines" Proc. Natl. Acad. Sci. USA 1989, 86, 3379.), and ras (Brown, D.; Yu, Z. P.; Miller, P., et at. "Modulation of ras Expression by Anti-Sense, Nonionic Deoxyoligonucleotide Analogs" Oncogene Res. 1989, 4, 243) oncogenes can be inhibited by their complementary antisense oligonucleotides.

The antisense approach has also been applied to antiviral chemotherapies. One of the most exciting targets for antisense inhibition of viral infection has been the HIV binding site with its obvious application to AIDS. (Matsukura, M.; Shinozuka, K.; Zon, G.; Mitsuya, H.; Reitz, M.; Cohen, J. S.; Broder, S. "Phosphorothioate Analogs of Oligodeoxynucleotides: Inhibitors of Replication and Cytopathic Effects of Human Immunodeficiency Virus" Proc. Natl. Acad. Sci. USA 1987, 84, 7706.; Agarwal, S.; Goodchild, J.; Civeira, M. P.; Thornton, A. T.; Satin, P.M.; Zamecnik, P. C. "Oligodeoxynucleotide Phosphoroamidates and Phosphorothioates as Inhibitors of Human Immunodeficiency Virus" Ibid. 1988, 85, 7079; and, Satin, P. M.; Agarwal, S.; Civeira, M. P.; Goodchild, J.; Ikeuchi, T.; Zamecnik, P. C. "Inhibition of Acquired Immunodeficiency Syndrome Virus by Oligodeoxynucleoside Methylphosphonates" Ibid. 1988, 85, 7448).

Consequently, as the role of nucleic acid tertiary structure (at both the DNA & RNA level) becomes better understood and appreciated, research will undoubtedly focus on the interaction of proteins (and perhaps other macromolecules) with specific nucleic acid sites. Here, molecular recognition goes beyond the usual 2-dimensional Watson-Crick/Hoogsteen base-pairing modes with tertiary structure playing an important role in the specificity of interaction. (Steitz, T. "Structural Studies of Protein-Nucleic Acid Interaction: The Sources of Sequence-Specific Binding" Quarterly Reviews of Biophysics 1990, 23, 3). There is a clear need to develop new antisense/antigene agents and/or sequence specific drug carriers that can be rationally "tailored" to the conformations of specific nucleic acid target structures. The resulting molecules could serve as the basis for novel therapeutic approaches to diseases like cancer and AIDS at the genetic level.

While it is possible to genetically engineer a cell to produce the required antisense mRNA, there is still a demand for synthetic antisense and antigene agents. However, the use of synthetic (exogenous) DNAs and RNAs has two major flaws associated with it. They are (1) the reluctance of polar, polyanionic species to cross lipid membranes (passively) and (2) the susceptibility of both DNA and RNA to inopportune degradation by cellular nucleases. Since both of these problems may be traced to the phosphodiester linkage, much effort has been devoted to devising an alternative backbone that would still accommodate the geometrical constraints of duplex and/or triplex formation.

In this regard, the methyl phosphonate (Miller, P. S. in Oligodeoxynucleotides. Antisense Inhibitors of Gene Expression, Cohen, J. S. Ed.; CRC Press: Boca Raton, Fla., 1989, Chapter 4) and phosphorothioate (Stein, C. A. in Ibid., Cohen, J. S. Ed.; CRC Press: Boca Raton, Fla., 1989, Chapter 5) groups (cf. A and B shown below) are examples of two of the more successful phosphodiester replacements that have been developed. On the other hand, a new problem arises with these two modifications in that they both render the phosphorous atom chiral which means that $2^n$ stereoisomers are possible for an oligomer with n linkages. Currently available options for circumventing this problem on a practical scale include the chromatographic resolution of diastereomeric dinucleoside H-phosphonates. (Seela, F.; Kretschmer, U. "Diastereomerically Pure $R_P$ and $S_P$ Dinucleoside H-Phosphonates: The Stereochemical Course of Their Conversion into P-Methylphosphonates, Phosphorothioates, and [$^{18}$O] Chiral Phosphates" J. Org. Chem. 1991, 56, 3861).

Examples of Known Nucleic Acid Surrogates.

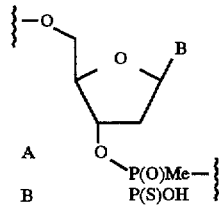

-continued

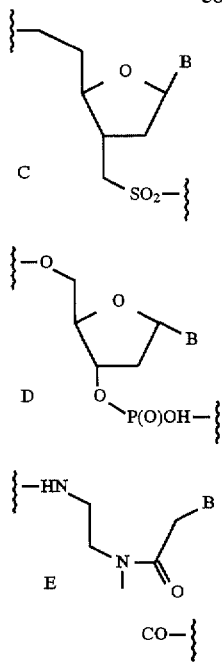

A number of research groups have looked at replacing the phosphodiester with a different (achiral) linkage altogether (cf. Benner's sulfone-based surrogate C above) but the utility of such oligomers as antisense inhibitors has yet to be fully demonstrated. (Huang, Z.; Schneider, K. C.; Benner, S. A. "Building Blocks for Oligonucleotide Analogues with Dimethylene Sulfide, Sulfoxide, and Sulfone Groups Replacing Phosphodiester Linkages" *J. Org. Chem.* 1991, 56, 3869). On the other hand, Imbach's group has shown that α-oligos like D above do bind to nucleic acids in a sequence specific manner though not always with the usual anti parallel strand alignment. (Rayner, B.; Malvy, C.; Paoletti, J.; Lebleu, B.; Paoletti, C.; Imbach, J.-L. in *Oligodeoxynucleotides. Antisense Inhibitors of Gene Expression*, Cohen, J. S. Ed.; CRC Press: Boca Raton, Fla., 1989, Chapter 6). Perhaps even more surprising are the results of Swedish workers who found sequence specific hybridization is possible with achiral peptide nucleic acids (PNAs) such as E where the ribose phosphate unit has been replaced by an achiral peptide-like repeat unit. (Egholm, M.; Buchardt, O.; Nielsen, P. E.; Berg, R. H. "Peptide Nucleic Acids (PNA). Oligonucleotide Analogues with an Achiral Peptide Backbone" *J. Am. Chem. Soc.* 1992, 114, 1895). These last two examples underscore the fact that while geometry is important for hybridization, departures from the native ribose phosphate backbone can be tolerated provided the key geometrical/H-bonding constraints are met.

As a result, there is considerable interest in developing oligonucleotide surrogates that are capable of maintaining Watson-Crick (Hoogsteen) base-pairing to native RNA (DNA) targets but do not incorporate the usual phosphodiester linkages which are susceptible to nucleases and incompatible with passive membrane transport. An interesting approach to this problem involves the use of backbones made up of peptide linkages which connect the base-containing subunits. Besides their obvious resistance to nucleases, such peptide nucleic acid (PNA) surrogates would also be amenable to block or solid phase peptide synthesis techniques.

The concept of peptide-based nucleic acid surrogates is itself not new. Jones and coworkers prepared polymers incorporating repeat unit 1 (B=T, n≈9–20) set forth below but found that they did not interact appreciably with polyadenylic acid (poly-A). (Jones, A. S. *Int. J. Biol. Macromol.* 1979, 1, 194; Buttrey, J. D.; Jones A. S.; Walker, R. T. *Tetrahedron* 1975, 31, 73). Shvachkin's group made a variety of well-defined homo- and heteronucleopeptides corresponding to 1 as well as "mixed" nucleopeptides incorporating subunit 2 and noted that the latter formed stable complexes with complementary duplexes. (Cf. Tyaglov, B. V.; Permogorov, V. I.; Chernykh, N. A.; Semiletov, Yu. A.; Konde, K.; Shvachkin, Yu. P. *Zh. Obshch. Khim.* 1987, 57, 2124, and references cited therein). De Konig and Pandit prepared nucleopeptides corresponding to 3 and 4 but found no interaction between poly-3 and poly-A. (De Koning, H.; Pandit, U. K. *Rec. Trav. Chim.* 1971, 91, 1069, and references cited therein). Polymers made up of the more complex unit 5, on the other hand, did show binding to their complementary nucleic acid sequences. (Takemoto, K.; Inaki, Y. *Polym. Mat. Sci. Eng.* 1988, 58, 250). More recently, Weller and coworkers reported the synthesis of nylon-based surrogates 6. (Huang, S.-B.; Nelson, J. S.; Weller, D. D. *J. Org. Chem.* 1991, 56, 6007) while Egholm et al demonstrated that oligomers made up of the achiral unit 7 form stable 2:1 complexes with complementary DNA. (Egholm, M.; Buchardt, O.; Nielsen, P. E.; Berg, R. H. *J. Am. Chem. Soc.* 1992, 114, 1895).

Peptide nucleic acid (PNA) structural repeat units.

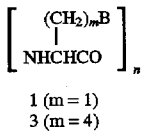

1 (m = 1)
3 (m = 4)

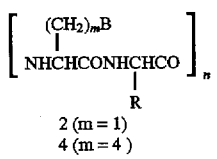

2 (m = 1)
4 (m = 4)

B = nucleotide

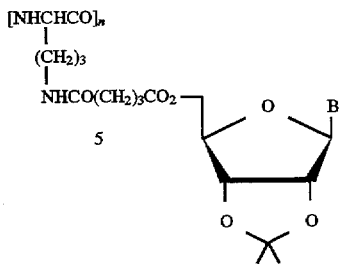

5

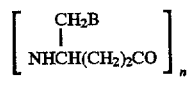

6

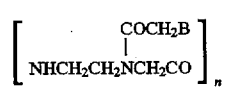

7

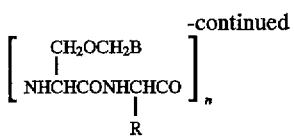

8

One of the drawbacks associated with systems 1 through 4 (as well as 6) is the need to synthesize the corresponding nucleoaminoacid building blocks in enantiomerically pure form. As a result, the present inventor felt that a novel nucleic acid surrogate 8 may offer some advantages in this respect since it incorporates readily available α-amino acids. Here, the nucleobase is attached to a serine residue via a hemiaminal linkage which preserves the natural N-glycoside (O—C—N) substructure. This connector provides an additional H-bond acceptor and lateral flexibility which may lead to better binding to certain nucleic acid structures. There is also the potential for attaching chemical probes, etc. onto the spacer amino acid or N-methylation to prevent degradation by proteases. Molecular modeling studies by Weller suggest that peptides 2 incorporating glycine spacers appear to be well-suited for binding to complementary nucleic acids within the B-helix motif. (Weller, D. D.; Daly, D. T.; Olsen, W. K.; Summerton, J. E. *J. Org. Chem.* 1991, 56, 6000). The inventor's own preliminary modeling studies indicated that repeat unit 8 can also accommodate the B-DNA helix conformation without undue steric strain. Molecular modeling was done using the Biograf 3.1 software package. Conformational sampling was achieved via quenched dynamics followed by all-atom E-minimization. Relative strain was deduced by comparing $E_{helix}-E_{free}$ for both B-PNA and B-DNA models.

Consequently, an object of the present invention is to develop a new class of nucleic acid surrogates capable of sequence specific binding to single stranded DNA and RNA as well as double stranded DNA targets. A further object of the invention is to utilize the new peptide-based nucleic acid surrogates as antisense/antigene probes and/or drug carriers.

These and other objects and features of the invention will be apparent from the following summary and description of the invention and from the claims.

SUMMARY OF THE INVENTION

In one aspect, the present invention is directed to the synthesis of new peptide-based nucleic acid surrogates incorporating repeating (Ser/Thr [CH₂B]-amino acid) subunits. These new peptide-based nucleic acid surrogates are believed to be capable of maintaining Watson-Crick (Hoogsteen) base-pairing to native RNA and DNA targets but do not incorporate the usual phosphodiester linkages which are susceptible to nucleases and incompatible with passive membrane transport.

The new peptide-based nucleic acid surrogates are generally defined by the Formula 1:

(Ser/Thr[CH₂B]-AA)ₙ         Formula 1 wherein B is a nucleobase (i.e. B=adenine, cytosine, guanine, thymine and uracil), AA is an alpha (α)-amino acid. In addition, Ser is serine and Thr is threonine. These are two aliphatic, polar amino acids that contain an alcoholic hydroxyl group.

In another aspect, the present invention relates to a peptide-nucleic acid (PNA) incorporating one or more (Ser [CH₂B]-AA) subunits herein B is a nucleobase (i.e. B=adenine, cytosine, guanine, thymine and uracil), AA is an alpha (α)-amino acid. More preferably, the peptide nucleic acid of the invention comprises multiple Ser[CH₂B]-Gly subunits.

In this regard, the peptide backbone of the peptide-based nucleic acid surrogates of the present invention is derived entirely from readily available α-amino acids and does not entail (the usually nontrivial) asymmetric carbon-carbon bond formation. This facilitates the development of the solid-phase (automated) chemical synthesis of oligomers possessing defined sequences of nucleobases. It has been found that peptide bond formation can be achieved with nucleobase-containing dipeptidyl repeat units without competing α-racemization or β-elimination.

In addition, in the present invention, the nucleobases (B=adenine, cytosine, guanine, thymine, & uracil) are attached to alternating serine or threonine residues via a (readily introduced) hemiaminal linkage which preserves the natural N-glycoside (O—C—N) substructure. This is believed to be an important molecular recognition element for effective binding to target nucleic acid sequences (or complementary regulatory proteins). There also exists the potential for attaching chemical probes onto the spacer amino acid. N-Alkylation of this residue could also be useful for the prevention of degradation by proteases.

Further scope of the applicability of the present invention will become apparent from the detailed description given hereinafter. It should, however, be understood that the detailed description and specific examples, while indicating preferred embodiments of the invention, are given by way of illustration only, since various changes and modifications within the spirit and scope of the invention will become apparent to those skilled in the art.

DETAILED DESCRIPTION OF THE INVENTION

The present invention relates to the development of a new class of oligonucleotide surrogates capable of sequence specific binding to single stranded DNA and RNA as well as to double stranded DNA targets. More specifically, structures (Ser/Thr[CH₂B]-AA)ₙ below represent the repeating structural units for a number of the nucleic acid surrogates of the present invention. Once synthesized (in suitably protected form), the monobasic units are linked together via peptide bonds to produce the required oligomeric structures having defined nucleobase sequences. These nucleic acid surrogates can then be utilized for use as antisense/antigene probes and/or drug carriers.

A summary of the inventor's work towards peptide nucleic acids (PNAs) corresponding to repeat unit 8 is presented in Schemes 1 and 2 below. In this regard, the inventors felt that oligomers based on 8 would offer some advantages over known PNAs since they would be simpler to synthesize and yet allow for the eventual attachment of chemical probes onto the "spacer" amino acid. In the inventor's system, the nucleobase (B) is attached to a serine or a threonine residue via a hemiaminal linkage which preserves the natural N-glycoside (O—C—N) substructure. Molecular modeling studies on this system (vide supra) indicated that repeat unit 8 can, indeed, accommodate the B-DNA helix conformation without undue steric strain.

More particularly, synthesis of monomeric building blocks BOC-Ser[CH₂B]OMe corresponding to all four natural nucleobases (B=A, C, G, & T) is shown in Scheme 1 below. All new compounds were characterized by IR, ¹H & ¹³C NMR, and HR FAB MS. The numbers set forth in the parenthesis relate to the identical compounds utilized in the Examples set forth further below.

First, the known L-serine derivative 9 (138) is converted to its methylthiomethyl (MTM) ether 10 (139) in good yield using the method of Kyler. Medina, J. C.; Salomon, M.; Kyler, K. S. *Tetrahedron Lett.* 1988, 29, 3773). This compound was coupled to silylated $N^6$-benzoyladenine ($A^{Bz}o2TMS$) (Huang, Z.; Schneider, K. C.; Benner, S. A. *J. Org. Chem.* 1991, 56, 3869.), $N^4$-benzoylcytosine. ($C^{Bz}o2TMS$) (Huang, S.-B.; Nelson, J. S.; Weller, D. D. *J. Org. Chem.* 1991, 56, 6007.), $N^2$-acetylguanine ($G^{Ac}o3TMS$) (Azuma, T.; Isono, K. *Chem. Pharm. Bull.* 1977, 25, 3347) and thymine (To2TMS) (Nishimura, T.; Iwai, I. *Chem. Pharm. Bull.* 1964, 12, 352) after activation with NBS (Sugimura, H.; Osumi, K.; Yamazaki, T.; Yamaya, T. *Tetrahedron Lett.* 1991, 32, 1813) to give the corresponding acyclic nucleosides 11 (144), 12 (145), 13 (146), 14 (147), 15 (148) and 16 (140) (see boxed information). The yields of purified nucleosides are in the range of 64–72% and, in the case of the purine bases, the $N^7$ & $N^9$ regioisomers were readily separated from each other by simple flash chromatography. For these N-acylated purines, regiochemical assignments were made ($^1H$ & $^{13}C$ NMR) by comparing the relative chemical shifts of H-8, C-4, C-5, C-8, & C-1'. It is noteworthy that these conditions for both MTM ether formation and nucleosidation are mild enough to tolerate the presence of an acid-sensitive BOC group. Alternative methods for both MTM ether formation (DMSO+$Ac_2O$, rt) (Ogilvie, K. K.; Ngen-ba, N.; Hamilton, R. G. *Can. J. Chem.* 1984, 62, 1622) and thioglycoside nucleosidation (BoTMS$_n$, NIS, TfOH, rt) (Knapp, S.; Shieh, W.-C. *Tetrahedron Lett.* 1991, 32, 3627) were found to be decidedly inferior with the inventors' substrates.

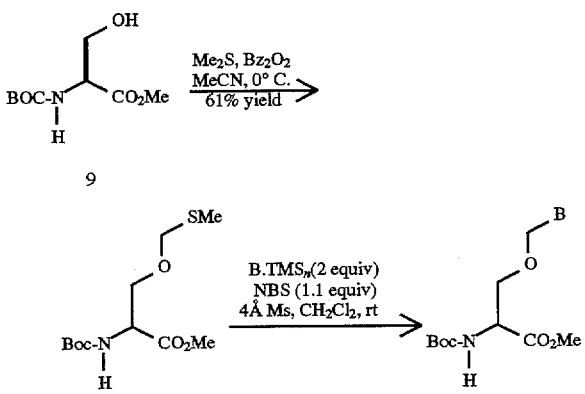

Scheme 1

Next, the peptide coupling protocol required for the synthesis of the PNAs of the present invention were determined that the novel aminoacid nucleosides produced could be incorporated into an oligopeptide structure of type 8 without racemization or β-elimination was demonstrated for the thymine series (Scheme 2 below). Peptide bond formation was best achieved using the p-nitrophenyl (PNP) active ester method. Thus, saponification of 16 (140) produced the carboxylic acid 17 (149) which was converted to its PNP ester 18 (150) and coupled directly with glycine methyl ester to give the dipeptide 19 (151) in 72% overall yield after chromatographic purification.

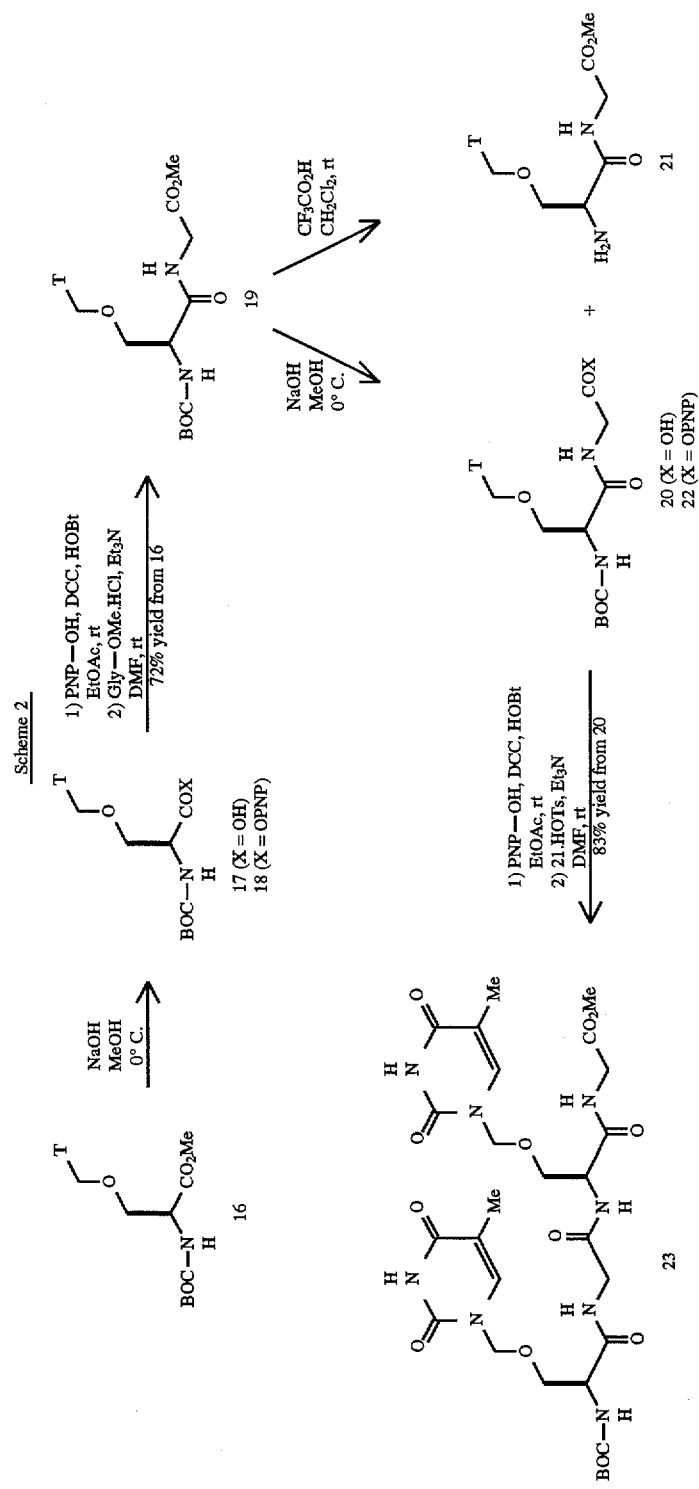

This compound served as the common building block for further peptide elongation as follows: Repetition of the saponification sequence with 19 (151) led to the dipeptide carboxylic acid 20 (152) whereas treatment of 19 (151) with trifluoroacetic acid (TFA) produced the complementary dipeptide amine 21 (153) which was isolated as its p-TsOH salt. Free acid 20 (152) was then activated as the PNP ester 22 (154) and coupled with the amine 21 (153) to give the tetrapeptide 23 (155) in 83% isolated yield after flash chromatography. The 400 MHz $^1$H NMR spectrum of this compound showed only traces of a possible diastereomer suggesting that racemization had been minimal.

Further reiteration is possible to elongate the chains to produce peptides of any desired length and sequences, although a solid phase synthesis may be more appropriate. In conclusion, the synthesis of building blocks 16 (140), 11 (144), 12 (145), 13 (146), 14 (147) and 15 (148) corresponding to four natural nucleobases (A,C,G,&T) was achieved and it was demonstrated that such units may be linked together using standard peptide coupling techniques without racemization or β-elimination.

The inventors have accomplished the synthesis of an octapeptide from the building block 19 (15 1) and the final hexadecapeptide can be prepared either via a convergent segment condensation or solid phase peptide synthesis in the future. The stage is now set for elongation of 23 (155) into oligopeptide structures and biophysical evaluation of their interaction with nucleic acid targets.

It is believed that the peptide nucleic acids (cf. structure 8) of the present invention have the following advantages over known peptide-based nucleic acid surrogates:

(1) It is possible to synthesize PNAs of defined configuration using standard solution and/or solid phase peptide coupling protocols starting from readily available amino acids (or simple derivatives thereof).

(2) The nucleobase can be attached to the serine residue via hemiaminal linkage which preserves the natural N-glycoside (O—C—N). The resulting H-bonding possibilities and lateral flexibility can lead to better recognition of certain nucleic acid structures.

(3) There is the potential for modification of the nucleic acid surrogate structure in response to structural requirements. The spacer amino acid can be modified to make the PNA more resistant to proteases and/or to allow for attachment of chemical probes.

The present invention is further illustrated by the following examples. It is to be understood that the present invention is not limited to the examples, and various changes and modifications may be made in the invention without departing from the spirit and scope thereof.

EXAMPLES

The peptide-based nucleic acid surrogates incorporating (Ser/Thr[CH$_2$B]-Gly) subunits were prepared as follows:
Preparation of Silylated Bases Silylated bases To2TMS, G$^{Ac}$o3TMS, C$^{Bz}$o2TMS, and A$^{Bz}$o2TMS were prepared from thymine, N$^2$-acetylguanine, N$^4$-benzoylcytosine, and N$^6$-benzoyladenine, respectively, according to literature procedures.

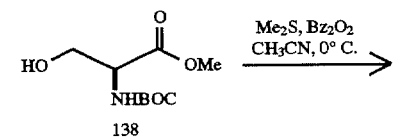

138

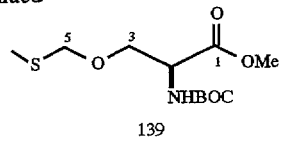

139

BOC-L-Ser(MTM)-OMe (139)

To a cold (0° C.) solution of BOC-L-Ser-OMe (138) (8.40 g, 38.3 mmol) in CH$_3$CN (150 mL) was added Me$_2$S (23.0 mL, 307 mmol) followed by the portionwise addition of Bz$_2$O$_2$ (37.0 g, 153 mmol) over a 30 min period. The reaction mixture was stirred at 0° C. for 4 h, at which time, TLC analysis showed the reaction was complete. The reaction mixture was diluted with Et$_2$O (700 mL), washed with 1 N NaOH (100 mL×2), brine (100 mL×2), dried over MgSO$_4$, then evaporated to give 40.8 g of residual solid. Remaining reagent and impurities were removed by Kugelrohr distillation and the resulting oil submitted to flash chromatography (SiO$_2$, 4:1 hexanes-EtOAc) to give pure BOC-L-Ser(MTM)-OMe (139) (6.5 g, 61% isolated yield) as a colorless oil. R$_f$ 0.52 (2:1 hexanes-EtOAc, char A); $[\alpha]^{26}_D$ −1.5° (c, 5.4 CHCl$_3$); IR (CHCl$_3$) 1760, 1680, 1630, 1590 cm$^{-1}$; $^1$H NMR (300 MHz, CDCl$_3$) δ5.34 (d, J=8.1 Hz, NHBOC), 4.63 (d, J=11.6 Hz, H-5a), 4.55 (d, J=11.7 Hz, H-5$_b$), 4.46 (m, H-2), 3.96 (dd, J=9.5, 3.1 Hz, H-3a), 3.74 (s, CO$_2$CH$_3$), 3.71 (dd, J=9.5, 3.2 Hz, H-3b), 2.06 (s, SCH$_3$), 1.42 (s, BOC); $^{13}$C NMR (75.4 MHz, CDCl$_3$) δ170.96, 155.35 (2×CO), 79.96 (CO$_2$C(CH$_3$)$_3$), 75.40 (C-4), 67.69 (C-3), 53.64 (C-2), 52.42 (CO$_2$CH$_3$), 28.23 (CO$_2$C(CH$_3$)$_3$), 13.61 (SCH$_3$); HRMS (FAB/glycerol) calcd for C$_{11}$H$_{21}$NO$_5$S (M$^+$) 279.1140, found 279.1084.

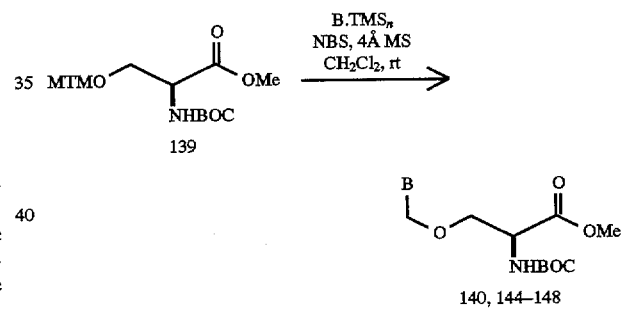

General Coupling Procedures

To a cold (0° C.) solution of 139, NBS (1.1 equiv) and 4 Å MS (0.25g/mmol of 139) in CH$_2$Cl$_2$ (0.1 M) was added a solution of silylated base (2 equiv, 0.66 M in CH$_2$Cl$_2$). The reaction mixture was stirred at room temperature until judged complete by TLC (30 rain to 1 h). The reaction mixture was diluted with CH$_2$Cl$_2$, washed with 10% NaHSO$_3$, brine, dried over MgSO$_4$, then evaporated to give the crude coupling products which were purified by flash chromatography (SiO$_2$).

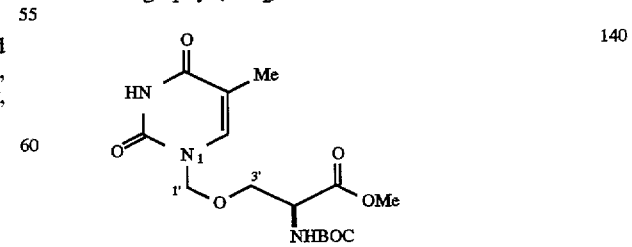

BOC-L-Ser(CH$_2$T)-OMe (140)

Flash chromatography (5:2 EtOAc-hexanes); 72% isolated yield; R$_f$ 0.39 (4:1 EtOAc-hexanes, char A); mp 131°–132° C. (from CH$_2$Cl$_2$-petroleum ether); [α]$^{21}_D$ –22.6° (c, 1.11 CHCl$_3$); IR (CHCl$_3$) 3000, 1750, 1710, 1690, 1500 cm$^{-1}$; $^1$H NMR (300 MHz, CDCl$_3$) δ9.01 (s, 3-NH), 7.05 (s, H-6), 5.34 (d, J=8.6 Hz, NHBOC), 5.12 (d, J=10.5 Hz, H-1'a), 5.07 (d, J=10.6 Hz, H-1'b), 4.44 (m, H-4'), 3.94 (dd, J=9.9, 3.3 Hz, H-3'a), 3.80 (dd, J=9.9, 3.3 Hz, H-3'b), 3.71 (s, CO$_2$CH$_3$), 1.91 (s, 5-CH$_3$), 1.41 (s, BOC); $^{13}$C NMR (75.4 MHz, CDCl$_3$) δ170.59, 155.25 (2×CO), 163.75 (C-4), 151.02 (C-2), 138.65 (C-6), 111.85 (C-5), 80.29 (CO$_2$C(CH$_3$)$_3$), 76.48 (C-1'), 69.55 (C-3'), 53.66 (C-4'), 52.65 (CO$_2$CH$_3$), 28.24 (CO$_2$C(CH$_3$)$_3$), 12.30 (5-CH$_3$); HRMS (FAB/glycerol) calcd for C$_{15}$H$_{23}$N$_3$O$_7$ (M$^+$) 357.1536, found 357.1542.

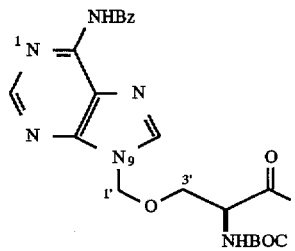 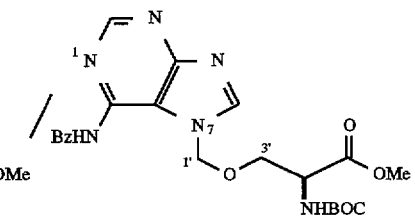

144 / 145

BOC-L-Ser(CH$_2$$^9$A$^{Bz}$)-OMe (144)/BOC-L-Ser(CH$_2$$^7$A$^{Bz}$)-OMe (145)

Flash chromatography (20:1 EtOAc-MeOH); 144: 32% isolated yield; R$_f$ 0.57 (14:1 EtOAc-MeOH, char A); [α]$^{22}_D$ –4.2° (c, 0.62 CHCl$_3$); IR (CHCl$_3$) 1745, 1705, 1610, 1500 cm$^{-1}$; $^1$H NMR (300 MHz, CDCl$_3$) δ9.18 (bs, NHBz), 8.82 (s, H-8), 8.13 (s, H-2), 8.34–7.51 (m, NHBz), 5.68 (s, H-1'a,b), 5.48 (d, J=8.4 Hz, NHBOC), 4.47 (m, H-4'), 4.00 (dd, J=9.6, 3.3 Hz, H-3'a), 3.87 (dd, J=9.7, 3.2 Hz, H-3'b), 3.67 (s, CO$_2$CH$_3$), 1.43 (s, BOC); $^{13}$C NMR (75.4 MHz, CDCl$_3$) δ170.38, 164.65, 155.28 (3×CO), 153.19 (C-6), 152.35 (C-2), 149.73 (C-4), 142.71 (C-8), 133.44, 132.88, 128.87, 127.93 (Ph), 122.68 (C-5), 80.33 (CO$_2$C(CH$_3$)$_3$), 72.92 (C-1'), 70.05 (C-3'), 53.57 (C-4'), 52.66 (CO$_2$CH$_3$), 28.24 (CO$_2$C(CH$_3$)$_3$); HRMS (FAB/glycerol) calcd for C$_{22}$H$_{26}$N$_6$O$_6$ (M$^+$) 470.1914, found 470.1975. 145: 33% isolated yield; R$_f$ 0.54 (14:1 EtOAc-MeOH, char A); [α]$^{20}_d$ –14° (c, 0.77 CHCl$_3$); IR (CHCl$_3$) 1740, 1700, 1600, 1415 cm$^{-1}$; $^1$H NMR (300 MHz, CDCl$_3$) δ8.34 (s, H-8), 8.17 (s, H-2), 8.29–7.46 (m, NHBz), 6.04 (d, J=10.1 Hz, H-1'a), 5.87 (d, J=10.1 Hz, H-1'b), 5.38 (d, J=7.7 Hz, NHBOC), 4.49 (m, H-4'), 4.15 (dd, J=9.5, 3.3 Hz, H-3'a), 4.01 (dd, J=9.7, 3.2 Hz, H-3'b), 3.67 (s, CO$_2$CH$_3$), 1.41 (s, BOC); $^{13}$C NMR (75.4 MHz, CDCl$_3$) δ175.78, 170.35, 155.31 (3×CO), 157.47 (C-4), 149.79 (C-2), 146.14 (C-6), 141.87 (C-8), 137.21, 132.44, 129.89, 128.31 (Ph), 114.92 (C-5), 80.42 (CO$_2$C(CH$_3$)$_3$), 77.63 (C-1'), 70.24 (C-3'), 53.77 (C-4'), 52.80 (CO$_2$CH$_3$), 28.27 (CO$_2$C(CH$_3$)$_3$); HRMS (FAB/glycerol) calcd for C$_{22}$H$_{26}$N$_6$O$_6$ (M$^+$) 470.1914, found 470.1888.

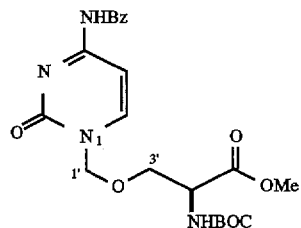

146

BOC-L-Ser(CH$_2$C$^{Bz}$)-OMe (146)

Flash chromatography (10:1 EtOAc-hexanes); 70% isolated yield; R$_f$ 0.60 (10:1 EtOAc-MeOH, char A); mp 69°–71° C.; [α]$^{25}_D$ –19.6° (c, 2.95 CHCl$_3$); IR (CHCl$_3$) 1745, 1710, 1670, 1625, 1480 cm$^{-1}$; $^1$H NMR (300 MHz, CDCl$_3$) δ9.06 (bs, NHBz), 7.94–7.51 (m, NHBz), 5.45 (d, J=8.4 Hz, NHBOC), 5.36 (d, J=10.1 Hz, H-1'a), 5.29 (d, J=10.4 Hz, H-1'b), 4.49 (m, H-4'), 4.06 (dd, J=9.6, 3.3 Hz, H-3'a), 3.91 (dd, J=9.7, 3.0 Hz, H-3'$_b$), 3.75 (s, CO$_2$CH$_3$), 1.44 (s, BOC); $^{13}$C NMR (75.4 MHz, CDCl$_3$) δ170.59, 162.86, 155.28 (3×CO), 166.50 (C-4), 155.31 (C-2), 147.28 (C-6), 133.26, 128.97, 128.80, 127.71 (NHCOC$_6$H$_5$), 97.57 (C-5), 80.22 (CO$_2$C(CH$_3$)$_3$), 78.32 (C-1'), 70.16 (C-3'), 53.70 (C-4'), 52.67 (CO$_2$CH$_3$), 28.24 (CO$_2$C(CH$_3$)$_3$,; HRMS (FAB/glycerol) calcd for C$_{21}$H$_{26}$N$_4$O$_7$ (M$^+$) 446.1801, found 446.1750.

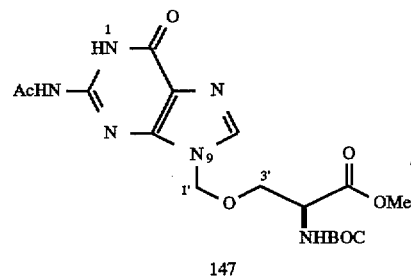 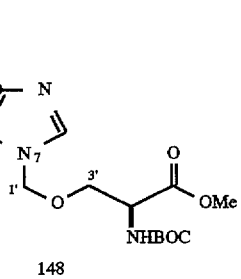

147 / 148

BOC-L-Ser(CH$_2$$^9$G$^{Ac}$)-OMe (147)/BOC-L-Ser(CH$_2$$^7$G$^{Ac}$)-OMe (148)

Flash chromatography (EtOAc to 20:1 EtOAc-MeOH); 147: 32% isolated yield; R$_f$0.35 (14:1 EtOAc-MeOH, char A); mp 130°–133° C.; [α]$^{23}_D$+14° (c, 0.85 CHCl$_3$); IR (CHCl$_3$) 1695, 1615, 1560, 1250 cm$^{-1}$; $^1$H NMR (300 MHz, CDCl$_3$) δ12.22 (S, 1-NH), 11.94 (s, 2-NHAc), 8.16 (d, J=8.8 Hz, NHBOC), 7.64 (s, H-8), 5.53 (d, J=8.4 Hz, H-1'a), 5.28 (d, J=8.5 Hz, H-3'b), 4.39 (bd, J=10.6 Hz, H-3'a), 4.28 (bd, J=8.8 Hz, H-4'), 3.83 (dd, J=10.7, 3.2 Hz, H-3'b), 3.74 (s, CO$_2$CH$_3$), 2.31 (s, 2-NHAc), 1.49 (s, BOC); $^{13}$C NMR (75.4 MHz, CDCl$_3$) δ173.22, 170.55, 155.25 (3×CO), 157.44 (C-6), 149.28 (C-2), 148.45 (C-4), 138.06 (C-8), 121.34

(C-5), 81.72 (CO$_2$C(CH$_3$)$_3$), 75.91 (C-1'), 69.36 (C-3'), 54.99 (C-4'), 54.72 (CO$_2$CH$_3$), 28.24 (CO$_2$C(CH$_3$)$_3$), 23.86 (NHCOCH$_3$); HRMS (FAB/glycerol) calcd for C$_{17}$H$_{24}$N$_6$O$_7$ (M$^+$) 424.1706, found 424.1693. 148: 32% isolated yield; R$_f$0.44 (14:1 EtOAc-MeOH, char A); mp 162°–164° C.; [α]$^{25}_D$–3.6° (c, 1.06 CHCl$_3$); IR (CHCl$_3$) 1690, 1610, 1500, 1365 cm$^{-1}$; $^1$H NMR (300 MHz, CDCl$_3$) δ12.41 (s, 1-NH), 11.01 (s, 2-NHAc), 7.95 (s, H-8), 5.76 (s, H-1'$_{a,b}$), 5.50 (d, J=8.4 Hz, NHBOC), 4.47 (m, H-4'), 4.04 (dd, J=9.5, 2.6 Hz, H-3'$_a$), 3.89 (dd, J=9.5, 2.5 Hz, H-3'b), 3.71 (s, CO$_2$CH$_3$), 2.42 (s, 2-NHAc), 1.43 (s, BOC); $^{13}$C NMR (75.4 MHz, CDCl$_3$) δ173.23, 170.60, 155.35 (3×CO), 156.76 (C-4), 153.06 (C-6), 148.18 (C-2), 143.65 (C-8), 111.96 (C-5), 80.22 (CO$_2$C(CH$_3$)$_3$), 75.59 (C-1') 69.32 (C-3'), 53.59 (C-4'), 52.66 (CO$_2$CH$_3$), 28.23 (CO$_2$C(CH$_3$)$_3$), 24.57 (NHCOCH$_3$); HRMS (FAB/glycerol) calcd for C$_{17}$H$_{24}$N$_6$O$_7$ (IV[$^+$]) 424. 1706, found 424.1736.

General Procedure for PNP Ester Synthesis

To a cold (0° C.) solution of N-BOC serine methyl ester derivative (0.5M in MeOH) was added 1N NaOH (2 equiv) and the reaction mixture was stirred at room temperature until judged complete by TLC (2 to 3 h). The reaction mixture was acidified to pH 2.5 with 1N HCl at 0° C. and extracted with 20% i-PrOH in EtOAc. The organic layer was washed with brine, dried over MgSO$_4$ then evaporated to give residue. When this residue was transferred to a smaller flask, MeOH should be used instead of 20% i-PrOH in EtOAc. Concentrated crude acid was coevaporated with benzene (3×) and the residue was pumped for 16 h. To a cold (0° C.) solution of p-nitrophenol (1.19 equiv), HOBt (0.5 equiv) and the crude acid prepared above in EtOAc (0.1M) was added a solution of DCC (1 equiv, 0.05M in EtOAc). The reaction mixture was stirred at room temperature until judged complete by TLC (4 to 16 h). The precipitate was filtered-off through a Celite and the filtrate evaporated and used for peptide coupling reaction without further purification.

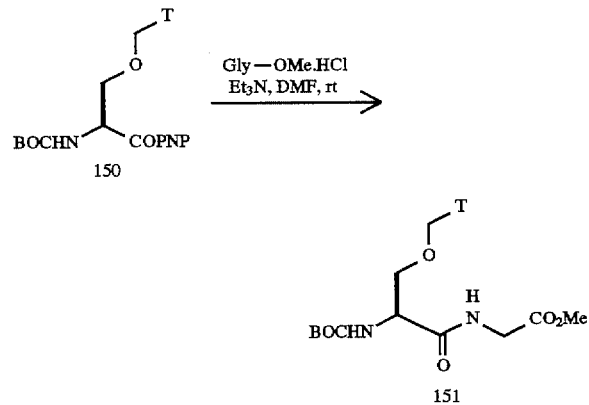

BOC-L-Ser(CH$_2$T)-Gly-OMe (151)

To a cold (0° C.) solution of glycine methyl ester HCl salt (2 equiv, 1M in DMF) was added Et$_3$N (40 equiv) and the reaction mixture was stirred at room temperature for 30 min. The solution of BOC-L-Ser(CH$_2$T)-Gly-OPNP (150) (0.05M in DMF) was added to the mixture and the reaction was stirred at room temperature for 3 h. All the volatiles were evaporated and the residue was co-evaporated with toluene (3×). The residual solid was submitted to flash chromatography (SiO$_2$, 97:3 EtOAc-MeOH) to give pure 151 (72% isolated yield). R$_f$ 0.30 (EtOAc, char A); mp 185°–186° C.; [α]$^{22}_D$+1.2° (c, 0.57 MeOH); IR (CHCl$_3$) 1750, 1700, 1610, 1415 cm$^{-1}$; $^1$H NMR (300 MHz, DMSO-d$_6$) δ11.31 (bs, 3'-NH), 8.33 (t, J=5.8 Hz, 6'-NH), 7.54 (s, H-6'), 6.93 (d, J=8.2 Hz, NHBOC), 5.04 (s, H-1a,b), 4.18 (m, H-4), 3.85–3.59 (m, H-3a,b, H-7a,b), 3.61 (S, CO$_2$CH$_3$), 1.76 (s, 5'-CH$_3$), 1.37 (s, BOC); $^{13}$C NMR (75.4 MHz, DMSO-d$_6$) δ170.00, 164.22, 155.16, 151.09, 140.43 (5×CO), 137.69 (C-6'), 109.14 (C-5'), 78.26 (CO$_2$C(CH$_3$)$_3$), 76.17 (C-1), 68.58 (C-3), 54.10 (C-4), 51.67 (CO$_2$CH$_3$), 40.59 (C-7), 28.12 (CO$_2$C(CH$_3$)$_3$), 11.89 (5'-CH$_3$); HRMS (FAB/glycerol) calcd for C$_{17}$H$_{26}$N$_4$O$_8$ (M$^+$) 414.1750, found 414.1716.

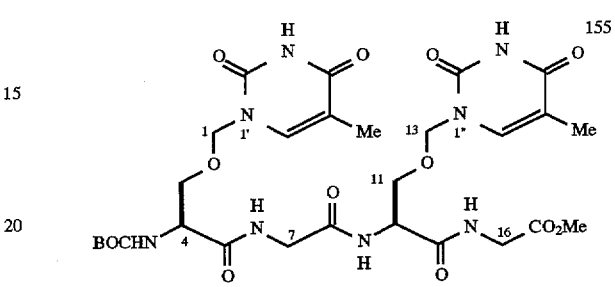

BOC-L-Ser(CH$_2$T)-Gly-L-Ser(CH$_2$T)-Gly-OMe (155) (SEQ ID NO:1)

To a solution of BOC-L-Ser(CH$_2$T)-Gly-OMe (151) (1.2 equiv, 0.02M in CH$_2$Cl$_2$) was added TFA (20 equiv) and the reaction mixture was stirred at room temperature for 2 h. All the volatiles were evaporated and the residue was dissolved in CHCl$_3$ and TsOH (1.4 equiv) was added. After 30 min, the reaction mixture was coevaporated with CHCl$_3$ (3×) and the residue was pumped for 16 h, then the residue was used for peptide coupling reaction without further purification. To a cold (0° C.) solution of free amine salt (1M in DMF) was added Et$_3$N (20 equiv) and the reaction mixture was stirred at room temperature for 30 min. A solution of BOC-L-Ser (CH$_2$T)-Gly-OPNP (154) (0.05M in DMF) was added to the mixture and the reaction was stirred at room temperature for 3 h, at which time, TLC analysis showed the reaction was complete. All the volatiles were evaporated and the residue was coevaporated with toluene (3×). The residual solid was submitted to flash chromatography (SiO$_2$, 9:1 EtOAc-MeOH) to give pure 155 (83% isolated yield). R$_f$0.49 (4:1 EtOAc-MeOH, char A); mp 120°–122° C.; [α]$^{22}_D$+3.4° (C, 1.02 MeOH); IR (CHCl$_3$) 1740, 1710, 1600, 1420 cm$^{-1}$; $^1$H NMR (300 MHz, DMSO-d$_6$) δ11.33 (s, 3'-NH & 3"-NH), 8.47 (t, J=5.6 Hz, 6-NH), 8.19 (d, J=7.9 Hz, 8-NH), 8.11 (t, J=5.6 Hz, 15-NH), 7.54 (s, H-6'), 7.52 (s, H-6"), 6.98 (d, J=8.0 Hz, 4-NHBOC), 5.04 (bs, H-1$_{a,b}$ & H-13a,b), 4.52 (m, H-10), 4.17 (m, H-4), 3.84–3.64 (m, H-3$_{a,b}$ & H-7$_{a,b}$ & H-11$_{a,b}$ & H-16a,b), 3.62 (s, CO$_2$CH$_3$), 1.76 (s, 5'-CH$_3$ & 5"-CH$_3$), 1.37 (s, BOC); $^{13}$C NMR (75.4 MHz, DMSO-d$_6$) δ169.92, 169.68, 169.47, 168.57, 164.20, 155.20, 151.09 (9×CO), 140.42, 140.28 (C-6', C-6"), 109.25, 109.15 (C-5', C-5"), 78.33 (CO$_2$C(CH$_3$)$_3$), 76.13 (C-1, C-13), 68.59, 68.49 (C-3, C-11), 54.22 (C-4), 52.34 (C- 10), 51.68 (CO$_2$CH$_3$), 41.94 (C-16), 40.59 (C-7), 28.10 (CO$_2$C(CH$_3$)$_3$), 11.87 (5'-CH$_3$, 5"-CH$_3$); HRMS (FAB/glycerol) calcd for C$_{28}$H$_{40}$N$_8$O$_{13}$ (M$^+$) 696.2715, found 696.2800.

The invention has been described with reference to the preferred embodiment. Obviously, modifications and alterations will occur to others upon a reading and understanding of the preceding detailed description. It is intended that the invention be construed as including all such alterations and modifications insofar as they come within the scope of the appended claims or the equivalents thereof.

---

Having thus described the invention, it is claimed:

1. A peptide-based nucleic acid surrogate comprises one or more Ser(CH$_2$B)-AA subunits having the following structural formula:

$$\left( \begin{array}{c} \text{B} \\ | \\ \text{CH}_2 \\ | \\ \text{O} \\ | \\ -\text{N}-\text{C}-\text{AA}- \\ | \quad \| \\ \text{H} \quad \text{O} \end{array} \right)_n$$

wherein B is a nucleobase, AA is an alpha-amino acid and n≧1.

2. The peptide-based nucleic acid surrogate according to claim 1 wherein the alpha-amino acid represented by the variable AA has the following structure:

$$\begin{array}{c} \text{H} \quad \text{O} \\ | \quad \| \\ -\text{N}-\text{C}-\text{C}- \\ | \\ \text{R} \end{array}$$

wherein R is an amino acid side chain and wherein the variable AA is attached to the peptide at the nitrogen atom of AA.

3. The peptide-based nucleic acid surrogate of claim 2 wherein R is H (Glycine).

4. The peptide-based nucleic acid surrogate of claim 1 wherein B=

(thymine), (cytosine)

5. The peptide-based nucleic acid surrogate of claim 1 wherein B=

(thymine), (cytosine), (adenine), (guanine), or (uracil)

6. The peptide-based nucleic acid surrogate of claim 1, wherein the amino terminus of said surrogate is covalently bonded to tert-butoxycarbonyl (BOC) and the carboxy terminus of said surrogate is covalently bonded to a methoxy group.

7. A peptide-based nucleic acid surrogate comprising one or more Thr(CH$_2$B)-AA subunits having the following structural formula:

where B is a nucleobase, AA is an alpha-amino acid and n≧1.

8. The peptide-based nucleic acid surrogate according to claim 7 wherein the alpha-amino acid represented by the variable AA has the following structure:

wherein R is an amino acid side chain and wherein the variable AA is attached to the peptide at the nitrogen atom of AA.

9. The peptide-based nucleic acid surrogate of claim 8 wherein R is H (Glycine).

10. The peptide-based nucleic acid surrogate of claim 7 wherein B=

(thymine), (cytosine), (adenine), (guanine), or (uracil)

11. The peptide-based nucleic acid surrogate of claim 1 wherein n is greater than 1.

12. The peptide-based nucleic acid surrogate of claim 7 wherein n is greater than 1.

13. A peptide-based nucleic acid surrogate comprising BOC-L-Ser(CH₂B)-Gly-L-Ser(CH₂B)Bly-OMe (SEQ ID NO:1) having the structure:
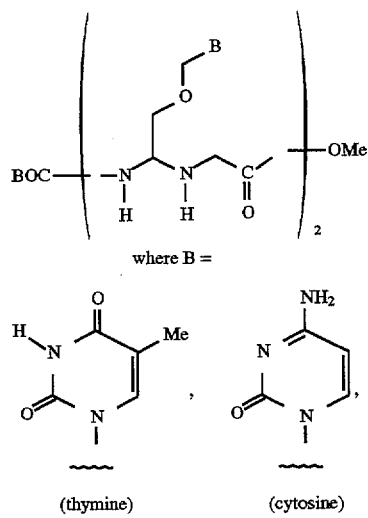
where B =
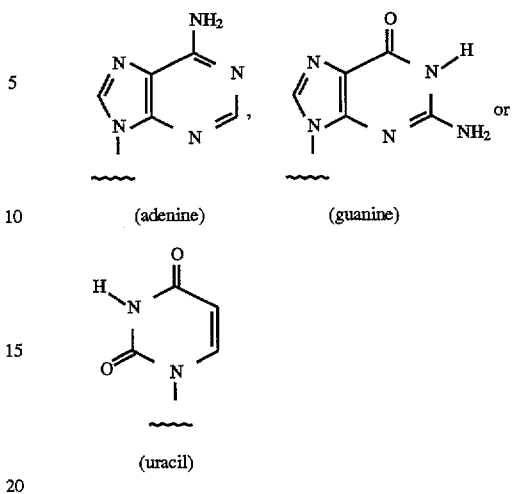
and BOC=tert-butoxycarbonyl.
* * * * *

UNITED STATES PATENT AND TRADEMARK OFFICE
CERTIFICATE OF CORRECTION

PATENT NO. : 5,731,416
DATED : March 24, 1998
INVENTOR(S) : Philip P. Garner

It is certified that error appears in the above-identified patent and that said Letters Patent is hereby corrected as shown below:

Column 1, before "Background of the Invention", please insert the following paragraph:
---This invention was made with government support under Grant No. NIH GM35557 awarded by the National Institutes of Health. The government has certain rights in this invention.---

Signed and Sealed this

First Day of February, 2000

Attest:

Q. TODD DICKINSON

*Attesting Officer*   *Acting Commissioner of Patents and Trademarks*